United States Patent [19]

Haber et al.

[11] Patent Number: 5,281,235
[45] Date of Patent: * Jan. 25, 1994

[54] NEEDLE MANIPULATOR

[75] Inventors: Terry M. Haber, Lake Forest; William H. Smedley, Lake Elsinore; Clark B. Foster, Laguna Niguel, all of Calif.

[73] Assignee: Habley Medical Technology Corporation, Laguna Hills, Calif.

[*] Notice: The portion of the term of this patent subsequent to Jan. 4, 2011 has been disclaimed.

[21] Appl. No.: 839,510

[22] Filed: Feb. 21, 1992

[51] Int. Cl.⁵ .................................. A61B 17/00
[52] U.S. Cl. .................................. 606/139; 606/144; 606/146; 606/148; 606/205; 606/207; 606/208
[58] Field of Search ............... 606/205–208, 606/139, 144, 145, 146, 147, 148; 81/385, 386, 387, 391, 392

[56] References Cited

U.S. PATENT DOCUMENTS

| | | | |
|---|---|---|---|
| 1,274,669 | 8/1918 | Bohn | 606/206 |
| 2,363,334 | 11/1944 | Jones | 606/147 |
| 2,365,647 | 12/1944 | Ogburn | 606/147 |
| 3,168,097 | 2/1965 | Dormia | 606/147 |
| 4,562,839 | 1/1986 | Blake. III et al. | 606/143 |
| 4,580,567 | 4/1986 | Schweitzer et al. | 606/207 |
| 4,643,190 | 2/1987 | Heimberger | 606/205 |
| 4,815,476 | 3/1989 | Clossick | 606/207 |
| 4,872,456 | 10/1989 | Hasson | 606/207 |
| 4,890,615 | 1/1990 | Caspari et al. | 606/146 |
| 4,935,027 | 6/1990 | Yoon | 606/148 |
| 5,084,054 | 1/1992 | Bencini et al. | 606/206 |
| 5,147,373 | 9/1992 | Ferzli | 606/144 |
| 5,176,702 | 1/1993 | Bales | 606/205 |

FOREIGN PATENT DOCUMENTS 0586661 3/1947 United Kingdom ............... 606/146

OTHER PUBLICATIONS

JARIT Laparoscopic Cholecystectomy Instruments. STAR 2000 Series, 1991.

*Primary Examiner*—Stephen C. Pellegrino
*Assistant Examiner*—Jeffrey A. Schmidt
*Attorney, Agent, or Firm*—Townsend & Townsend Khourie & Crew

[57] ABSTRACT

A needle manipulator (2), particularly suited for endoscopic use, has an elongate body (4) including a base (6) and an elongate tip carrier tube (8) rotatably mounted to the base. A removable tip assembly (10), mounted at the distal end of the tip carrier tube, includes jaws (26,28) actuated by finger and thumb loops (16,18) mounted to the base. A rotary actuator trigger (78) is slidably mounted to the base. The tip carrier tube has a spiral groove (90) engaged by a cam pin (82) extending from the trigger so that axial movement of the trigger causes rotary motion of the tip carrier tube and the tip assembly therewith. Suture material (93) is supplied through the carrier tube and to a needle (118) held by the jaws.

17 Claims, 8 Drawing Sheets

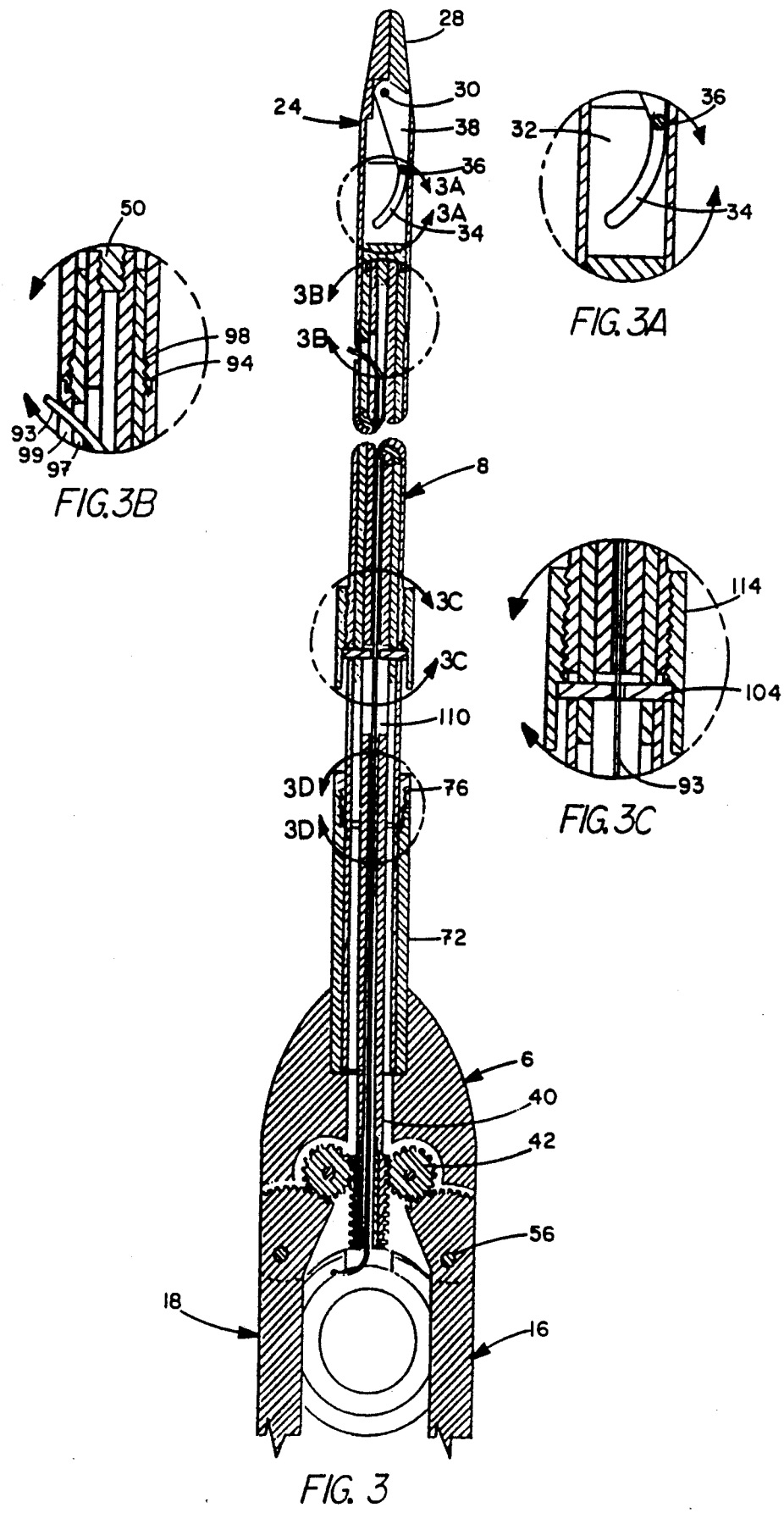

NEEDLE MANIPULATOR

BACKGROUND OF THE INVENTION

Endoscopic surgery is widely used because it is much less traumatic than conventional open surgery. With endoscopic surgery, an incision is made in the patient's body and a port is passed through the incision. Various types of endoscopic instruments are passed through the port and appropriate procedures are carried out.

One type of endoscopic instrument is forceps specially configured to grasp objects and cut tissue. Conventional forceps typically use scissors-type of thumb and finger holes offset to one side of the axis in a pistol griptype of arrangement. Such forceps, although well designed for cutting and simple grasping tasks, are not particularly suited for manipulating a needle during endoscopic procedures.

SUMMARY OF THE INVENTION

The present invention is directed to a needle manipulator, specially suited for use during endoscopic surgery, which permits the user to rotate the jaws grasping the needle through axial manipulation of a finger actuated trigger.

The needle manipulator has an elongate body including a base and an elongate tip carrier rotatably mounted to the base. A, preferably removable, tip assembly is mounted at the distal end of the tip carrier. The removable tip assembly includes movable jaws which are coupled with a pair of thumb and finger loops mounted to the proximal end of the body by a drive rod. The thumb and finger loops are preferably located on opposite sides of the axis of the elongate body. The thumb and finger loops move the drive rod axially, preferably through the engagement of gear teeth on the thumb and finger loops and on the drive rod.

A rotary actuator trigger is preferably slidably mounted to the proximal end of the body. The tip carrier has, in the preferred embodiment, a spiral groove at a proximal end thereof. The spiral groove is engaged by a cam pin mounted to the rotary actuator trigger so that axial movement of the rotary actuator trigger causes rotary motion of the tip carrier and the tip assembly therewith. This permits the user to clamp a suturing needle between the jaws and rotate the needle through one-handed manipulation: the jaws are opened and closed using one's thumb and middle finger while the jaws are rotated using one's index finger.

A supply of suture material can be mounted to the trigger. The suture material can be directed up through the tip carrier, passed out through a side port in the tip carrier and supplied to the needle held by the jaws.

The invention provides several advantages over conventional grasping forceps. The jaw rotator assembly permits the user to rotate the needle holding jaws by pulling or pushing on the rotary actuator trigger. Incorporating the jaws as part of a removable tip assembly allows a single needle manipulator to be used with a number of tip assemblies to accommodate different specific types, sizes or shapes of needles and other objects. The jaw actuating thumb and finger loops are positioned so that they lie on opposite sides of the axis of the manipulator. This allows the user to rotate the needle manipulator by rotating one's wrist. In contrast, with the prior art pistol-type handles, rotation of the instrument about its axis is more difficult and less precise.

Other features and advantages of the invention will appear from the following description in which the preferred embodiment has been set forth in detail in conjunction with the accompanying drawings.

BRIEF DESCRIPTION OF THE DRAWINGS

FIG. 3 is a cross-sectional view of a portion of the needle manipulator of FIG. 1 with the jaws in a closed position;

FIGS. 3A-3D show portions of the needle manipulator of FIG. 3 enlarged to show detail;

DESCRIPTION OF THE PREFERRED EMBODIMENT

Figure 1:
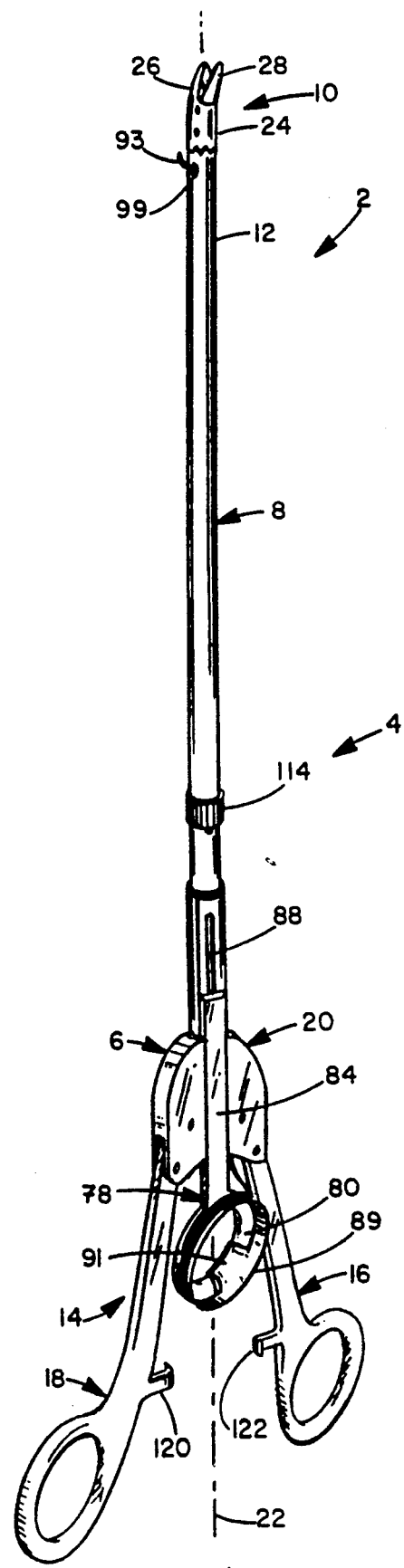
FIG. 1 is an overall perspective view of a needle manipulator made according to the invention.

FIG. 1 illustrates a needle manipulator 2 including an elongate body 4, the body including a base 6 and an elongate tip carrier tube 8. Manipulator 2 also includes a tip assembly 10 mounted to the distal end 12 of tube 8 and a jaw driver assembly 14. Jaw driver assembly 14 is used to manipulate the jaws carried by the tip assembly as is described below through the opening and closing of jaw actuating finger and thumb loops 16, 18. Manipulator 2 further includes a jaw rotator assembly 20 used to rotate tip carrier tube 8 and tip assembly 10 therewith about the longitudinal axis 22 of the manipulator.

Figure 2:
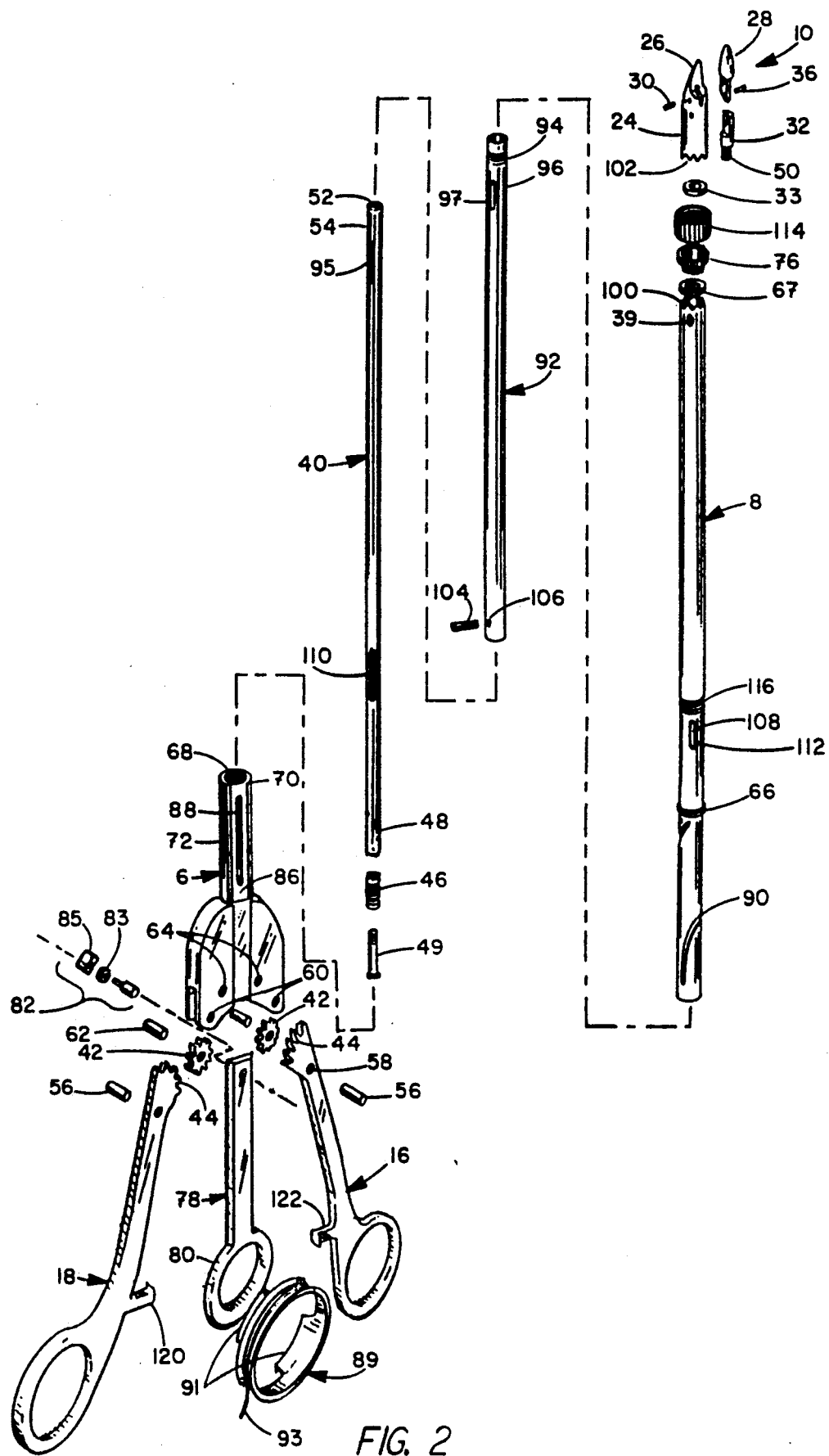
FIG. 2 is an exploded isometric view of the needle manipulator of FIG. 1.
Figure 3D:
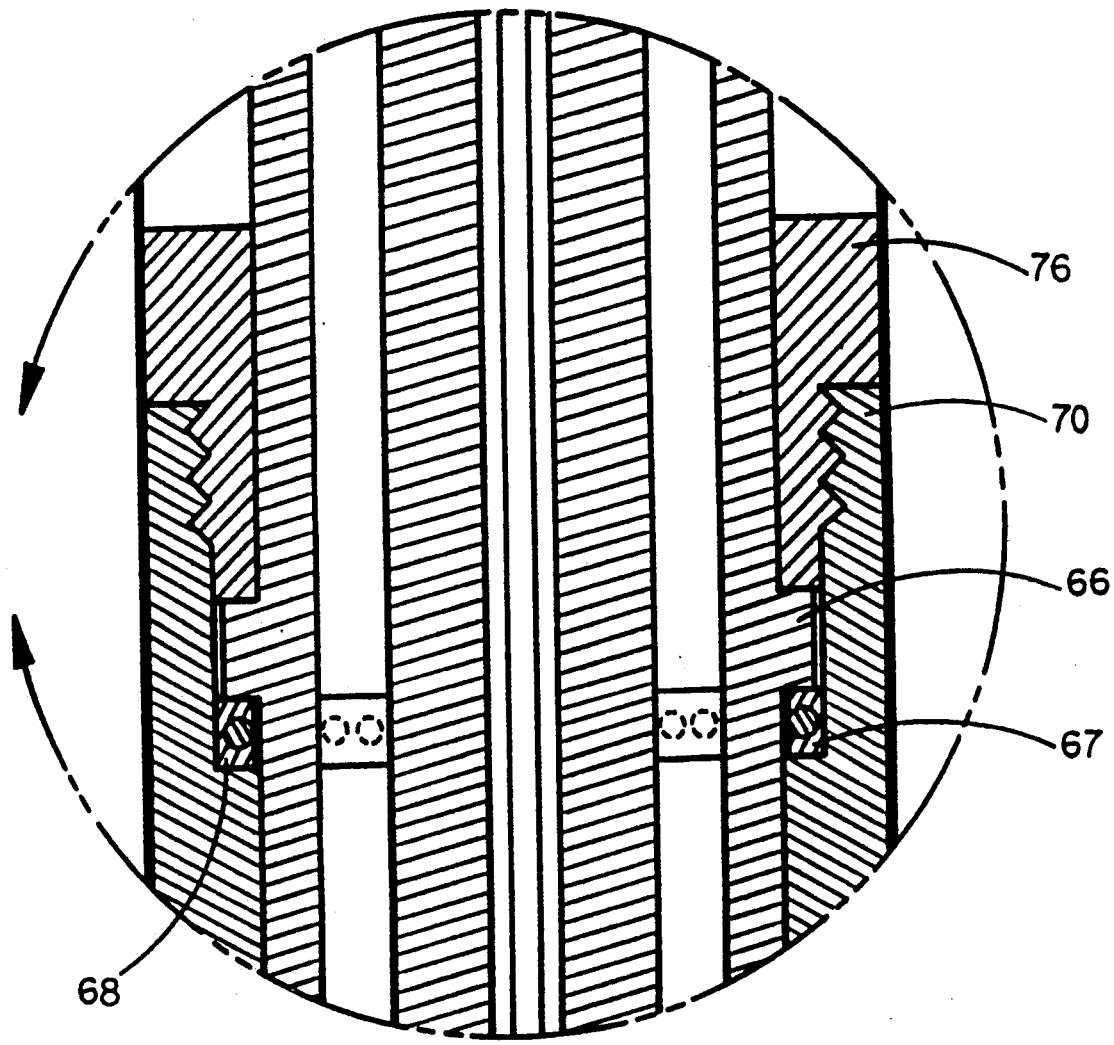
Figure 4:
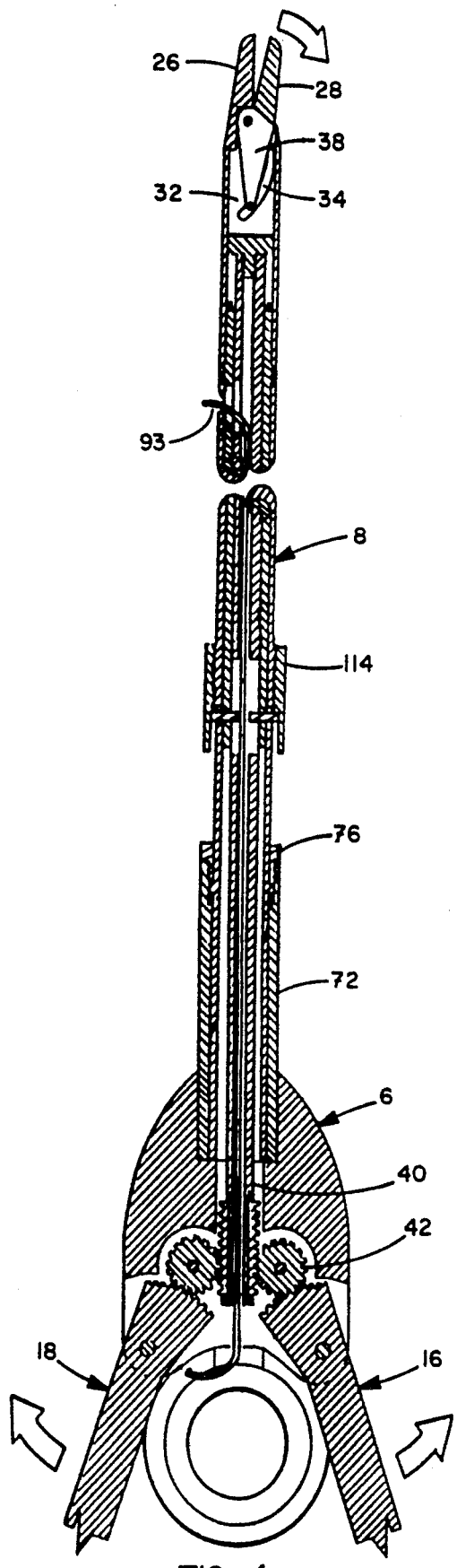
FIG. 4 shows the needle manipulator of FIG. 3 with the jaws in the open position.
Figure 5:
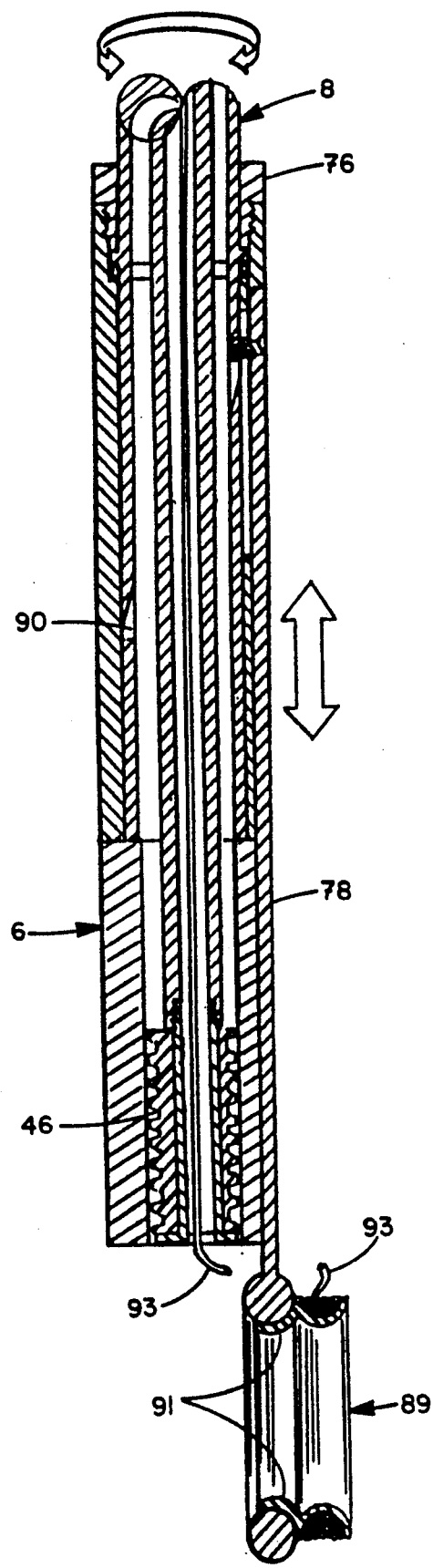
FIG. 5 is a cross-sectional view of a portion of the needle manipulator of FIG. 1 taken in a plane perpendicular to the plane of FIG. 3.

FIG. 2 illustrates tip assembly 10 as including a tip 24 having a fixed jaw 26 integral with tip 24 and a movable jaw 28 secured to tip 24 by a pivot pin 30. Tip assembly 10 also includes an adapter 32 sized to fit within and slide within the hollow interior of tip assembly 10. Adapter is held within the interior of tip 24 by a ring 33 press fit into the tip interior. Adapter 32 has a cam slot 34 within which a drive pin 36 extending from an end 38 of movable jaw 28 rides. Thus, axial movement, that is movement parallel to axis 22, of adapter 32 causes movable jaw 28 to move from the closed jaw position of FIG. 3 to the open jaw position of FIG. 4. This is accomplished by the manipulation of jaw driver assembly 14. (See FIG. 1)

Jaw driver assembly 14 includes finger and thumb loops 16, 18 coupled to an axial drive rod 40 through the engagement of idler gears 42 with drive gear segments 44 formed on finger and thumb loops 16, 18 and a rotary rack 46 formed on the proximal end of 48 of drive rod 40. Rack 46 is secured to end 48 by a screw 49 to permit rack 46 to rotate freely. Adapter 32 includes a threaded tip 50 which engages a threaded hole 52 at the distal end of 54 of rod 40. Finger and thumb loops 16, 18 are pivotally mounted to base 6 through the use of pivot pins 56 passing through pivot holes 58 formed in loops 16, 18 and pivot pin bores 60 formed in base 6. Idler gears 42 are secured to base 6 by idler gear pins 62 which pass through bores in the idler gears and through idler gear pin holes 64 in base 6.

Tip carrier tube 8 has an annular shoulder 66 sized and positioned to seat against a thrust bearing 67 supported by an internal annular surface 68 formed at the distal end 70 of barrel portion 72 of base 6. See FIG. 3D. The proximal end 74 of tube 8 is maintained within base 6 by an externally threaded ring 76. Ring 76 is sized so that when the ring is secured against distal end 70 of barrel portion 72, tube 8 is securely mounted to base 6 but is free to rotate within the base. Thrust bearing 67 helps to ensure the free rotation of tube 8 during use.

Jaw rotator assembly 20 includes a rotary actuator trigger 78 having a finger loop 80 at its proximal end and a cam pin 82 at its distal end. Trigger 78 incudes elongate portion 84 having a dovetail or trapezoidal cross-sectional shape which slides within a similarly configured dovetail slot 86 formed along the length of base 6. Pin 82 passes through an axial slot 88 formed in barrel portion 72 along slot 86. Pin 82 passes through slot 88 to engage a spiral groove 90 formed in proximal end 74 of tube 8. Pin 82 includes a ring 83 which rides within slot 88 and a guide 85 which rides within spiral groove 90, both ring 83 and guide 85 preferably made of PTFE. Thus, axial movement of trigger 78 causes pin 82 to ride along spiral groove 90, thus rotating tube 8 and tip assembly 10 therewith about axis 22.

Tip assembly 10 is secured to tip carrier tube 8 using a hollow tip mounting tube 92. Tip mounting tube 92 has external threads 94 at its distal end 96 which engage internal threads 98 formed within the interior of tip 24. Tip 24 and tip carrier tube 8 have opposed, complementary tooth surfaces 100, 102 which, when engaged, keep tip assembly 10 from rotating relative to tip carrier tube 8. Tube 8, mounting tube 92 and drive rod 40 are secured to one another by a common pin 104. Pin 104 passes through a bore 106 in mounting tube 92, a short slot 108 in carrier tube 8 and a long slot 110 in drive rod 40. Common pin 104 is maintained at the proximal end 112 of slot 108, thus keeping tooth surfaces 102, 100 engaged, through the use of an internally threaded ring 114 threaded onto external threads 116 formed on the outside of tube 8 adjacent slot 108. Slot 110, being longer than slot 108, can still move axially through the manipulation of finger and thumb loops 16, 18, thus causing jaws 26, 28 to open and close.

A suture material supply spool 89 is mounted to finger loop 80 through the use of snap flanges 91 which engage the inside of the finger loop. Suture material 93 is directed from needle 118, through hole 99 in tube 8, through slots 95, 97 in rod 40 and tube 92, through the center of rod 40 and is wound about spool 89.

The operation of needle manipulator 2 will now be described. The user places his or her thumb and middle finger through thumb and finger loops 18, 16. Loops 18, 16 are separated, as suggested in FIG. 4, causing drive gear segments 44 to rotate idler gears 42 which, in turn, drive rotary rack 46 axially, that is parallel to axis 22. This causes adapter 32 to move axially so that drive pin 36 moves along cam slot 34, thus opening jaws 26, 28 through the pivotal movement of movable jaw 28. A needle 118 is placed between jaws 26, 28 and is secured in place by moving finger loops 16, 18 back towards one another to the position of FIGS. 1 and 3. Needle 118 is locked between jaws 26, 28 through the engagement of catches 120, 122 carried by loops 16, 18. The manipulation of rotary actuator trigger 78 parallel to axis 22 causes pin 82 to ride along spiral groove 90, thus rotating tip carrier tube 8 and tip assembly 10 therewith about axis 22. Tip mounting tube 92 and axial drive rod 40 are likewise rotated about axis 22 upon the actuation of trigger 78 due to the interlocking engagement of common pin 104 with all three members. With needle manipulator 2, the user's hand, wrist and arm can be generally aligned with axis 22 for enhanced control.

Figure 6:
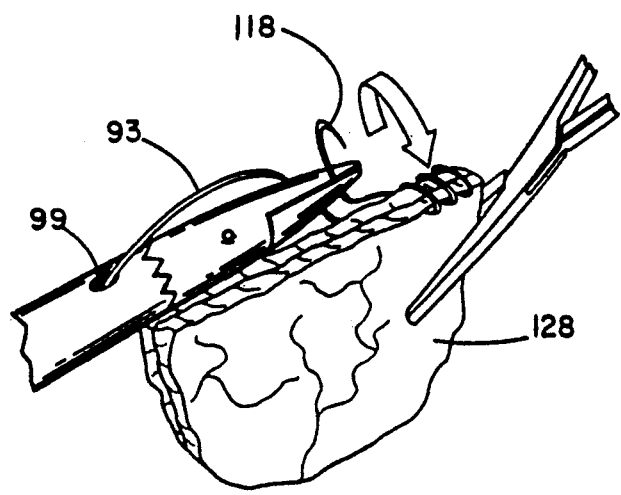
FIG. 6 is an enlarged view of the tip assembly of FIG. 1 shown manipulating a needle to suture tissue.
Figure 6A:
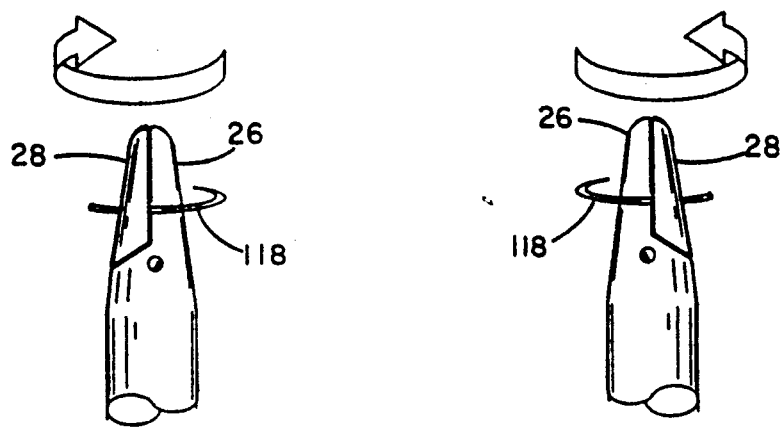
FIGS. 6A and 6B illustrate the rotary movement of the tip assembly and needle of FIG. 6 as the trigger is pulled and pushed, respectively.
Figure 6A:
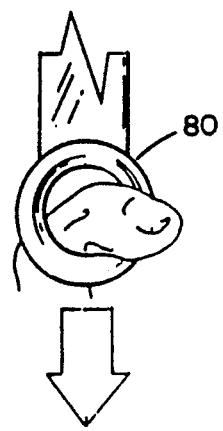
Figure 6B:
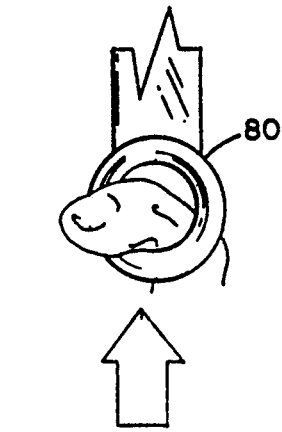
Figure 7:
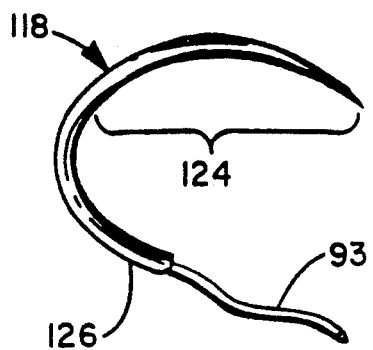
FIGS. 7 and 7A are enlarged plan and side views of the needle of FIG. 6 showing the attachment of the suture material and the special shape of the needle.
Figure 7A:
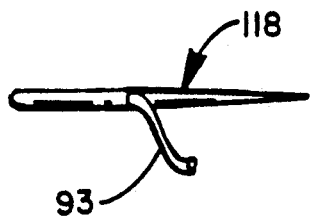
Figure 7B:
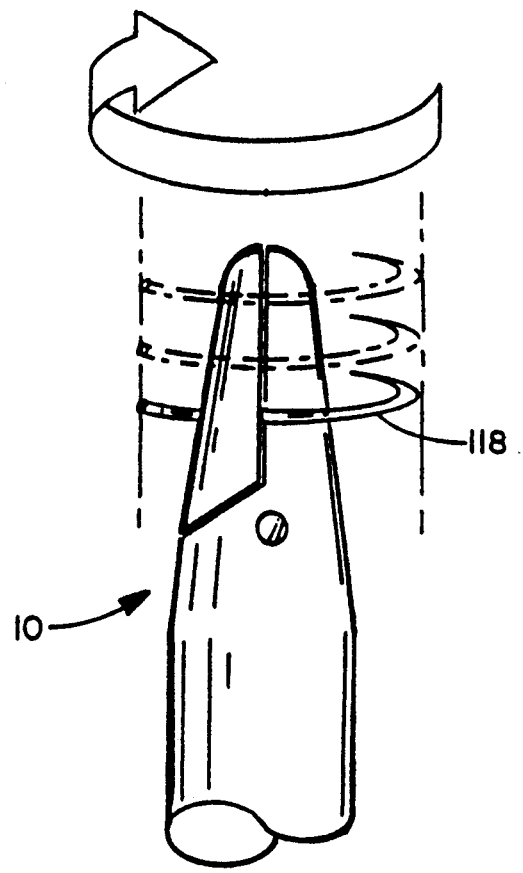
FIG. 7B illustrates the progression of the needle of FIG. 6 after successive stitches caused by rotation of the tip assembly and needle.

The reciprocal movement of trigger 78 causes tip assembly 10 and needle 93 to move in opposite rotary directions. See FIGS. 6, 6A and 6B. In the preferred embodiment this movement is through an arc of about 240°. Only when needle 93 is moved in the appropriate rotary direction, clockwise in FIG. 6, will the needle pierce tissue 128. After the piercing movement, the user releases needle 118 from between jaws 26, 28, rotates tip assembly 10 in the opposite direction, regrasps needle 118 between jaws 26, 28, pulls needle 118 completely through tissue 128, repositions needle 118 between jaws 26, 28 at a position 126 along the needle and repeats the process.

Needle 118 has a generally elliptical shape with a main portion 124 having a generally circular shape. Needle 118 can be grasped between jaws 26, 28 at a position 126 adjacent the attachment point for suture material. Point 126 is located at about the center of the generally circular arc formed by a main portion 124 so that when tip assembly 10 is rotated about axis 22, main portion 124 moves along a generally circular path. This minimizes trauma to tissue 128 and makes the procedure easier to perform.

Modification and variation can be made to the disclosed embodiment without departing from the subject of the invention as defined in the following claims. For example, both jaws could be movable, rather than just having one movable. Other methods for mounting tip assembly to the remainder of the device could be used as well. It may be desired to spring bias loops 16, 18 away from one another and trigger 78 towards the position of FIG. 1.

What is claimed is:

1. A needle manipulator comprising:
   a longitudinal body having a base, a distal end and a proximal end defining a length therebetween;
   first and second jaws at the distal end of the body, at least the first jaw being movable relative to the second jaw between open and closed jaw positions;
   a jaw driver assembly including a user manipulatable jaw actuator, movably mounted to the proximal end of the body, and an axial driver assembly coupling the jaw actuator to at least the first jaw so that when the user manipulates the jaw actuator the first jaw moves relative to the second jaw between the open and closed jaw positions;
   the jaw actuator including jaw actuating finger and thumb elements pivotally mounted to the body, the finger and thumb elements being pivotally coupled to one another; and
   a jaw rotator including a user manipulatable rotary actuator slidably mounted to the body and being slidable along a substantially linear path, and a rotary driver drivingly coupling the rotary actuator and the first and second jaws so that sliding of the rotary actuator along the substantially linear path causes the first and second jaws to rotate in unison.

2. The needle manipulator of claim 1 wherein the body defines an axis passing through the distal and proximal ends and the finger and thumb elements are positioned on opposite sides of the axis.

3. The needle manipulator of claim 1 wherein the body includes a base and a hollow tip carrier tube rotatably mounted to the base, and the axial drive assembly includes an axial drive rod extending through the hollow tip carrier tube.

4. The needle manipulator of claim 1 wherein the jaws are part of a tip assembly, the tip assembly being removably mounted to the body.

5. A needle manipulator comprising:
a body having a distal end and a proximal end;
first and second jaws at the distal end of the body, at least the first jaw being movable relative to the second jaw between open and closed jaw positions;
a jaw driver assembly including a user manipulatable jaw actuator, movably mounted to the proximal end of the body, and an axial driver assembly coupling the jaw actuator to at least the first jaw, so that when the user manipulates the jaw actuator the first jaw moves relative to the second jaw between the open and closed jaw positions;
wherein the jaw actuator includes jaw actuating finger and thumb elements pivotally mounted to the body, the finger and thumb elements includes drive gear segments and the axial driver assembly includes an axial drive rod having a rack at a proximal end hereof coupled to the drive gear segments; and
a jaw rotator including a user manipulatable rotary actuator, movably mounted to the proximal end of the body, and a rotary driver, drivingly coupling the rotary actuator and the first and second jaws, so that user manipulation of the rotary actuator causes the first and second jaws to rotate in unison.

6. The needle manipulator of claim 5 wherein the axial driver assembly includes idler gears coupling the rack and the drive gear segments.

7. A needle manipulator comprising:
a body having a distal end, a proximal end, a base, and a tip carrier tube rotatably mounted to the base, the tip carrier tube being rotatable about an axis;
first and second jaws at the distal end of the body, at least the first jaw being movable relative to the second jaw between open and closed jaw positions;
a jaw driver assembly including finger and thumb elements pivotally mounted to the body and positioned on opposite sides of the axis, and an axial driver assembly coupling the finger and thumb elements to at least the first jaw, the finger and thumb elements being rotatably coupled so that the finger and thumb elements rotate together both toward and away from the axis, wherein rotation of the finger and thumb elements moves the first jaw relative to the second jaw between the open and closed jaw positions; and
a jaw rotator including a user manipulatable rotary actuator movably mounted to the proximal end of the body, and rotary driver, drivingly coupling the rotary actuator and the first and second jaws, so that user manipulation of the rotary actuator causes the first and second jaws to rotate in unison.

8. The needle manipulator of claim 7 wherein the jaws are part of a tip assembly, the tip assembly being removably mounted to the tip carrier tube.

9. A needle manipulator comprising:
a body having a distal end a proximal end, the body including a base and a tip carrier tube rotatably mounted to the base;
first and second jaws at the distal end of the body, at least the first jaw being movable relative to the second jaw between open and closed jaw positions;
a jaw driver assembly including a user manipulatable jaw actuator, movably mounted to the proximal end of the body, and an axial driver assembly coupling the jaw actuator to at least the first jaw, so that when the user manipulates the jaw actuator the first jaw moves relative to the second jaw between the open and closed jaw positions;
a jaw rotator including a user manipulatable rotary actuator, movably mounted to the proximal end of the body, and rotary driver, drivingly coupling the rotary actuator and the first and second jaws, so that user manipulation of the rotary actuator causes the first and second jaws to rotate in unison;
the rotary actuator including a rotary actuator finger element slidably mounted to the base and the tip carrier tube includes a spiral groove, the rotary actuator finger element having a cam pin slidably engaging the spiral groove so that linear movement of the rotary actuator finger element causes the cam pin to move along the spiral groove formed in the tip carrier tube, thereby rotating the tip carrier tube and the jaws mounted hereto; and
wherein the jaws are part of a tip assembly, the tip assembly being removably mounted to the tip carrier tube by a tip mounting tube housed within and secured to the tip carrier tube.

10. A needle manipulator comprising:
a longitudinal body having a distal end and a proximal end and defining a length therebetween with a first maximum dimension perpendicular to the length;
first and second jaws at the distal end of the body, least the first jaw being movable relative to the second jaw between open and closed jaw positions;
a jaw driver assembly including a user manipulatable jaw actuator, movably mounted to the proximal end of the body, and an axial driver assembly coupling the jaw actuator to at least the first jaw, so that when the user manipulates the jaw actuator the first jaw moves relative to the second jaw between the open and closed jaw positions;
a jaw rotator including a user manipulatable rotary actuator, movably mounted to the proximal end of the body, and a rotary driver, drivingly coupling the rotary actuator and the first and second jaws, so that user manipulation of the rotary actuator causes the first and second jaws to rotate in unison;
the longitudinal body having a hollow interior extending along a substantial portion of the length; and
means for supplying suture material to the distal end of the body through the hollow interior of the body.

11. A needle manipulator comprising:
a body having a distal end and a proximal end, the body including a hollow interior extending along a substantial portion of the length;

a tip assembly removably mounted to the distal end of the body;

the tip assembly including a first and second jaws, at least the first jaw being movable relative to the second jaw between open and closed jaw positions;

a jaw driver assembly including a user manipulatable jaw actuator, movably mounted to the proximal end of the body, and an axial driver assembly coupling the jaw actuator to at least the first jaw, so that when the user manipulates the jaw actuator the first jaw moves relative to the second jaw between the open and closed jaw positions;

the jaw actuator including jaw actuating finger and thumb elements pivotally mounted to the body, the body defining an axis passing through the distal and proximal ends and the finger and thumb elements being positioned on opposite sides of the axis;

a jaw rotator including a user manipulatable rotary actuator, movably mounted to the proximal end of the body, and a rotary driver, drivingly coupling the rotary actuator and the first and second jaws, so that user manipulation of the rotary actuator causes the first and second jaws to rotate in unison; and means for supplying suture material to the distal end of the body through the hollow interior of the body.

12. A needle manipulator comprising:

a longitudinal body having distal and proximal ends and defining a length therebetween;

jaws mounted to the distal end of the body for relative movement between open and closed positions;

user actuated means for moving at least one of the jaws between the open and closed positions;

the moving means including jaw actuating finger and thumb elements pivotally mounted to the body for movement towards and away from one another, finger and thumb elements being rotatably coupled to one another so that the finger and thumb elements pivot simultaneously in opposite directions; and user actuated means for rotating the jaws in unison about an axis passing through the distal and proximal ends of the body including a user manipulatable rotatory actuator slidably mounted to the body and being slidable along a substantially linear path, the rotatory actuator being operably coupled to the jaws so that sliding of the actuator along the substantially linear path rotates the jaws in unison.

13. The needle manipulator of claim 12 wherein the distal and proximal ends of the body define an axis and the finger and thumb elements are positioned on opposite sides of the axis.

14. A needle manipulator comprising:

a longitudinal body having distal and proximal ends and defining a length therebetween with a first maximum dimension perpendicular to the length;

jaws mounted to the distal end of the body for relative movement between open and closed positions;

user actuated means for moving at least one of the jaws between the open and closed positions;

user actuated means for rotating the jaws in unison about an axis passing through the distal and proximal ends of the body; and the longitudinal body having a hollow interior extending along a substantial portion of the length; and means for supplying suture material to the distal end of the body through the hollow interior of the body.

15. A needle manipulator comprising:

a longitudinal body having distal and proximal ends with an axis defined by the distal and proximal ends, the longitudinal body defining a length therebetween with a first maximum dimension perpendicular to the length and including a hollow interior extending along a substantial portion of the length;

a tip assembly removably mounted to the distal end of the body;

the tip assembly including first and second jaws, at least the first jaw being movable relative to the second jaw between open and closed jaw positions, the first and second jaws having a second maximum dimension perpendicular to the length when the first and second jaws are in the closed jaw position, the second maximum dimension of the jaws being no greater than the first maximum dimension of the body;

user actuated means for moving at least the first jaw between the open and closed jaw positions;

the moving means including jaw actuating finger and thumb elements movably mounted to the body and positioned on opposite sides of the axis;

user actuated means for rotating the jaws in unison about said axis; and means for supplying suture material to the distal end of the body through the hollow interior of the body.

16. A needle manipulator comprising:

a longitudinal body having a base, a distal end and a proximal end defining a length therebetween;

first and second jaws at the distal end of the body, the second jaw being fixed to the body, the first jaw being movable relative to the body and to the second jaw between open and closed jaw positions;

a jaw driver assembly including a user manipulatable jaw actuator, movably mounted to the proximal end of the body, and an axial driver assembly coupling the jaw actuator to at least the first jaw so that when the user manipulates the jaw actuator the first jaw moves relative to the second jaw between the open and closed jaw positions; and a jaw rotator including a user manipulatable rotary actuator slidably mounted to the body and being slidable along a substantially linear path, and a rotary driver drivingly coupling the rotary actuator and the first and second jaws so that sliding of the rotary actuator along the substantially linear path causes the first and second jaws to rotate in unison.

17. A needle manipulator comprising:

a longitudinal body having distal and proximal ends and defining a length therebetween;

jaws mounted to the distal end of the body for relative movement between open and closed positions, the jaws being part of a tip assembly removably mounted to the distal end of the body;

user actuated means for moving at least one of the jaws between the open and closed positions; and user actuated means for rotating the jaws in unison about an axis passing through the distal and proximal ends of the body including a user manipulatable rotatory actuator slidably mounted to the body and being slidable along a substantially linear path, the rotatory actuator being operably coupled to the jaws so that sliding of the actuator along the substantially linear path rotates the jaws in unison.

* * * * *